US009499454B2

(12) United States Patent
Deshpande et al.

(10) Patent No.: US 9,499,454 B2
(45) Date of Patent: *Nov. 22, 2016

(54) REDUCTIVE DEHYDROXYLATION OF VICINAL POLYOLS TO OLEFINS USING AN IODINE-BASED CATALYST HAVING ENHANCED SOLUBILITY

(71) Applicant: DOW GLOBAL TECHNOLOGIES LLC, Midland, MI (US)

(72) Inventors: Raj Deshpande, Pune (IN); Paul Davis, Pune (IN); Vandana Pandey, Pune (IN); Nitin Kore, Solapur (IN)

(73) Assignee: Dow Global Technologies LLC, Midland, MI (US)

( * ) Notice: Subject to any disclaimer, the term of this patent is extended or adjusted under 35 U.S.C. 154(b) by 164 days.

This patent is subject to a terminal disclaimer.

(21) Appl. No.: 14/364,696

(22) PCT Filed: Dec. 5, 2012

(86) PCT No.: PCT/US2012/067831

§ 371 (c)(1),
(2) Date: Jun. 12, 2014

(87) PCT Pub. No.: WO2013/090071

PCT Pub. Date: Jun. 20, 2013

(65) Prior Publication Data

US 2014/0378729 A1 Dec. 25, 2014

Related U.S. Application Data

(60) Provisional application No. 61/570,952, filed on Dec. 15, 2011.

(51) Int. Cl.
*C07C 1/22* (2006.01)

(52) U.S. Cl.
CPC ............ *C07C 1/22* (2013.01); *C07C 2523/04* (2013.01); *C07C 2527/06* (2013.01); *C07C 2527/08* (2013.01); *C07C 2527/24* (2013.01)

(58) Field of Classification Search
CPC .......... C07C 1/22; C07C 11/04; C07C 11/02
See application file for complete search history.

(56) References Cited

U.S. PATENT DOCUMENTS 5,516,960 A * 5/1996 Robinson ................. C07C 1/20 568/671
8,546,625 B2 10/2013 Peterson et al.
2007/0215484 A1 9/2007 Peterson et al.
2008/0179194 A1 7/2008 Robinson
2008/0216391 A1 9/2008 Cortright et al.
2009/0299109 A1 12/2009 Gruber et al.
2010/0069691 A1 3/2010 Morschbacker
2010/0076233 A1 3/2010 Cortright et al.
2010/0077655 A1 4/2010 Bauldreay et al.

OTHER PUBLICATIONS

Bradbury, "The Mechanism of the Reaction between Glycerol and Hydriodic Acid" Journal of the American Chemical Society 1952 74 (11), 2709-2712.*
Korshak, et al, High-molecular weight compounds. XXVIII. Action of hydriodic acid on ethylene glycol and its polyesters,Izvestiya Akademii Nauk SSSR, Seriya Khimicheskaya (1950) 276-7 CODEN: whole document.
Patterson et al, CXCVII.—The Decomposition of Ethylene Bromide by Potassium Iodide and Sodium Iodide Solutions.1862, 54, 517.
Iodine (Wikipedia), edited by Materialscientist Dec. 2011.
Arceo, et al., in "Rhenium-Catalyzed Didehydroxylation of Vicinal Diols to Alkenes Using a Simple Alcohol as a Reducing Agent," Journal of the American Chemical Society (JACS) Communications, Jul. 29, 2020), vol. 132-33, p. 11409.
Sarmah, et al., in "Regioselective Transformation of Allylic, Benzylic and Tertiary Alcohols into the Corresponding Iodides with Aluminum Triiodide: Deoxygenation of Vicinal Diols," Tetrahedron (1989), vol. 45, No. 11 pp. 3569-3574 pp. 3569-3574.
Ziegler, et al., in Inorganic Chemistry, vol. 48 (2008), pp. 9998-10000.
Barua, et al., A New Method for Deoxygenation of Vicinal Diols, Tetrahedron Letters, (1982) vol. 23, No. 13 pp. 1365-1366.
PCT/US2012/067831 International Search Report and Written Opinion, mailed Feb 26, 2013.
PCT/US2012/067831, International Preliminary Report on Patentability, mailed Mar. 26, 2014.
Office Action dated Aug. 1, 2016 pertaining to European Patent Application No. 12799492.9.

* cited by examiner

*Primary Examiner* — In Suk Bullock
*Assistant Examiner* — Jason Chong
(74) *Attorney, Agent, or Firm* — Dinsmore & Shohl LLP

(57) ABSTRACT

Olefins may be produced by the reductive dehydroxylation of vicinal polyols and/or their respective esters, in an aqueous reaction medium, under a hydrogen atmosphere, under suitable conditions, and in the presence of a halogen-based, preferably iodine-based, catalyst, wherein a solubility enhancing agent is employed to increase the solubility of the iodine-based catalyst in the aqueous reaction medium.

9 Claims, No Drawings

REDUCTIVE DEHYDROXYLATION OF VICINAL POLYOLS TO OLEFINS USING AN IODINE-BASED CATALYST HAVING ENHANCED SOLUBILITY

This application is a non-provisional application claiming priority from the U.S. Provisional Patent Application No. 61/570,952, filed on Dec. 15, 2011, entitled "REDUCTIVE DEHYDROXYLATION OF VICINAL POLYOLS TO OLEFINS USING AN IODINE-BASED CATALYST HAVING ENHANCED SOLUBILITY," the teachings of which are incorporated by reference herein as if reproduced in full hereinbelow.

This invention relates generally to the field of reductive dehydroxylation of polyols and their respective esters, especially vicinal polyols. More particularly, it is a process to accomplish such reductive dehydroxylation of such vicinal polyols using an iodine-based catalyst having enhanced solubility.

Sugar alcohols include a variety of diols and polyols. Such are frequently encountered in the form of mixtures of these materials, often including, for example, ethylene glycol, propylene glycol, glycerol, sorbitol, and a variety of other polyols containing from two to six carbon atoms. While sugar alcohols often represent viable starting materials for a variety of commercially useful products, such as olefins, the difficulty in separating them from one another may make it consequently difficult to control the selectivity to the desired final product or product mix.

Researchers have addressed conversions of alcohol mixtures in many ways. For example, United States Patent Publication (US) 2007/0215484 (Peterson, et al.) relates to a method of making hydrocarbons from polyalcohols (also known as "polyhydric alcohols" or "polyols") and carbohydrates (e.g., monosaccharides such as glucose, disaccharides such as sucrose, starches including polymers of alpha-D-glucose units such as amylase and amylopectin, and fibers such as cellulose-based polysaccharide fibers). The polyalcohols and carbohydrates are combined with hydroiodic acid (HI) in aqueous solution in an electrochemical cell to form the hydrocarbon and elemental iodine ($I_2$). A parallel reaction within the electrochemical cell reduces the $I_2$ to regenerate HI by reducing elemental iodine.

US 2008/0179194 (Robinson) teaches a coupled electrochemical system and method for its use wherein a polyol feed (e.g., biomass polyol containing feed) is reduced in a reducing solution including HI and a metal ion capable of converting (reducing) $I_2$ to HI during polyol reduction to hydrocarbon. Conversion occurs by way of an electrochemical reaction wherein a reduced metal ion selected from vanadium II ion ($V^{2+}$), europium II ion ($Eu^{2+}$) and titanium II ion ($Ti^{2+}$) is oxidized to its oxidized state with conversion back to its reduced state, regenerating HI.

US 2010/0076233 (Cortright, et al.) teaches processes and reactor systems for conversion of an oxygenated hydrocarbon, especially a water-soluble oxygenated hydrocarbon, to a paraffin used as a liquid fuel. The teachings include converting a water-soluble oxygenated hydrocarbon to an oxygenate (e.g., an alcohol, furan, ketone, aldehyde, carboxylic acid, diol, triol or another polyol), then dehydrating the oxygenate to an olefin. The deoxygenation catalyst is preferably a heterogeneous catalyst that comprises at least one metal on a catalyst support. The metals include one or more of Cu, Re, Fe, Ru, Ir, Co, Rh, Pt, Pd, Ni, Os, W, Ag and Au. The catalyst may also include one or more of Mn, Cr, Mo, V, Nb, Ta, Ti, Zr, Y, La, Sc, Zn, Cd, Sn, Ge, P, Al, Ga, In and Tl. See also US 2008/0216391 (Cortright, et al.).

US 2009/0299109 (Gruber, et al.) focuses on dehydration of alcohols derived from a renewable material, e.g., by fermentation or chemical conversion of biomass. Dehydration occurs using a heterogeneous or homogeneous acidic catalyst. Illustrative catalysts include an acid treated aluminum oxide catalyst and a sulfonic acid cation exchange catalyst.

Patent Cooperation Treaty Publication (WO) 2008/103480 (Peterson, et al.) relates to conversion of sugars, biomass or both to hydrocarbons, syngas or other compounds. The conversion includes forming alcohols or carboxylic acids from biomass and subjecting the alcohols, acids or both to decarboxylation (for carboxylic acids) or dehydration (for alcohols) using a metal catalyst, a metal ion catalyst, or a base catalyst. Decarboxylation catalysts include bases such as sodium hydroxide; oxidizing agents such as hydrogen peroxide; hydrogen; metal catalysts (e.g., iron or nickel); acid catalysts (e.g., hydrochloric acid, sulfuric acid or dissolved carbon dioxide); and metal ion (e.g., copper) catalysts.

E. Arceo, et al., in "Rhenium-Catalyzed Didehydroxylation of Vicinal Diols to Alkenes Using a Simple Alcohol as a Reducing Agent," *Journal of the American Chemical Society* (*JACS*) *Communications*, Vol. 132-33, p. 11409 (29 Jul. 2020), teach use of an alcohol, such as 5-nonanol, 3-octanol or 2-octanol, to enhance conversion of a vicinal diol, such as 1,2-tetradecanediol, to an olefin using dirhenium decacarbonyl as a catalyst.

P. Sarmah, et al., in "Regioselective Transformation of Allylic, Benzylic and Tertiary Alcohols into the Corresponding Iodides with Aluminum Triiodide: Deoxygenation of Vicinal Diols," *Tetrahedron*, Vol. 45, No. 1-1 (1989), pp. 3569-3574, teach use of a stoichiometric amount of aluminum triiodide as a catalyst to convert vicinal diols to olefins.

N. Barua, et al., in "A New Method for Deoxygenation of Vicinal Diols," *Tetrahedron Letters*, Vol. 23, No. 13 (1982), pp. 1365-1366, discusses conversion of cis- and trans-vicinal diols into olefins in a one-step reaction using a combination of chlorotrimethylsilane and sodium iodide, with sodium iodide being present in an amount in excess of what stoichiometry would indicate is necessary.

J. Ziegler, et al., in *Inorganic Chemistry*, Vol. 48 (2008), pp. 9998-10000, provides for use of methyltrioxorhenium in catalytic conversion of epoxides and vicinal diols to olefins with $H_2$ as a reductant.

J. Hine, et al., in "The Mechanism of the Transformation of Vicinal Dihalides to Olefins by Reaction with Iodide Ion," *Journal of the American Chemical Society*, Vol. 77 (1955), p. 365, discusses conversion of vicinal dihalides, such as 1,2-dibromobutane, to olefins by reaction with a stoichiometric amount of an iodide ion, for example, the amount that present in a solution of potassium iodide in methanol).

Despite the many approaches to similar or related problems, there remains a need for simple and economical processes to convert vicinal polyols and related compounds to olefins.

In one aspect, this invention provides a process for preparing an olefin, comprising subjecting a material selected from the group consisting of a vicinal polyol, an ester of a vicinal polyol, and combinations thereof, to reductive dehydroxylation in the presence of an iodine-based catalyst containing at least one iodine atom per molecule thereof, under conditions including the presence of gaseous hydrogen at a pressure of from 1 pound per square inch gauge (~6.89 kilopascals) to 2000 pound per square inch gauge (~13.79 megapascals), a temperature ranging from 50° C. to 250° C., an aqueous reaction medium, and a ratio of moles of the material to moles of the iodine atoms ranging from 1:10 to 100:1; wherein the iodine-based catalyst has partial solubility in the aqueous reaction medium and the partial solubility is enhanced by adding to the aqueous reaction medium a solubility enhancing agent; such that an olefin is formed.

A particular feature of the present invention is use of a catalyst that is iodine-based. As defined herein, the term "iodine-based" means that the catalyst contains at least one iodine atom and ionizes at least partially in an aqueous solution by losing one proton. It is important to note that the definition of "iodine-based" is applied to the catalyst at the point at which it catalyzes the dehydroxylation of the material. Thus, it may be formed in situ in the liquid reaction medium as or beginning with, for example, elemental iodine ($I_2$), or it may be introduced into the reaction as an iodide, for example, as pre-prepared HI. Non-limiting examples include iodine ($I_2$), hydroiodic acid (HI), iodic acid ($HIO_3$), lithium iodide (LiI), sodium iodide (NaI), and combinations thereof. The term "catalyst" is used in the conventionally understood sense, to clarify that the iodine-based catalyst takes part in the reaction but is regenerated thereafter and does not become part of the final product. The iodine-based catalyst is at least partially soluble in the liquid reaction medium.

For example, in one non-limiting embodiment where HI is selected as the iodine-based catalyst, it may be prepared as it is frequently prepared industrially, i.e., via the reaction of $I_2$ with hydrazine, which also yields nitrogen gas, as shown in the following equation.

$$2I_2+N_2H_4\rightarrow 4HI+N_2 \quad \text{[Equation 1]}$$

When performed in water, the HI must then be separated, via means such as distillation. Alternatively, HI may be distilled from a solution of NaI or another alkali iodide in concentrated hypophosphorous acid. Another way to prepare HI is by bubbling hydrogen sulfide steam through an aqueous solution of iodine, forming hydroiodic acid (which can then be distilled) and elemental sulfur (which is typically filtered).

$$H_2S+I_2\rightarrow 2HI+S \quad \text{[Equation 2]}$$

Additionally, HI can be prepared by simply combining $H_2$ and $I_2$. This method is usually employed to generate high purity samples.

$$H_2+I_2\rightarrow 2HI \quad \text{[Equation 3]}$$

Those skilled in the art will be able to easily identify process parameters and additional methods to prepare HI and/or other reagents falling within the scope of the invention. It is noted that sulfuric acid will not generally work for preparing HI as it will tend to oxidize the iodide to form elemental iodine.

As used herein the term "material" is used to define the compound being converted by the action of the catalyst in the presence of the gaseous hydrogen under the reductive dehydroxylation conditions. This compound may be a vicinal polyol, an ester of a vicinal polyol, or a combination thereof. This vicinal polyol may have any number of carbon atoms, but in preferred embodiments has from 2 to 12 carbon atoms; more preferably from 2 to 8 carbon atoms; and most preferably from 2 to 6 carbon atoms. The term "vicinal" means that the polyol has hydroxyl groups on adjacent carbons, and the total number of hydroxyl groups may vary according to the number of backbone carbons. Non-limiting examples of such may include ethylene glycol, propylene glycol, ethylene glycol diacetate, glycerol, glycerol diacetate, glycerol triacetate, and combinations thereof as mixtures. Such may be intentionally manufactured or purchased as a starting material, or may be a byproduct of another manufacturing process.

The amounts of the material and the catalyst are desirably proportioned for optimized conversion to the olefin or olefins. Those skilled in the art will be aware without further instruction as to how to determine such proportions, but generally a ratio of moles of material to moles of iodine atoms ranging from 1:10 to 100:1 is preferred. More preferred is a ratio ranging from 1:1 to 100:1; still more preferably from 4:1 to 27:1; and most preferably from 4:1 to 8:1.

Because the solubility of the iodine-based catalyst in the aqueous reaction medium is relatively low (less than 0.0011 mole of iodine atoms is soluble per liter of water at 20° C.) and because during the course of the reaction the starting material, if not $I_2$, converts to $I_2$ and is later reconverted to the original compound (e.g., HI) as shown in the reaction scheme hereinabove, it is desirable in the invention to include therein a solubility enhancing agent. Such may be any compound that enhances the solubility of the iodine-based catalyst in the aqueous reaction medium, but is preferably selected from iodide salts such as, for example, potassium iodide (KI), sodium iodide (NaI), lithium iodide (LiI), and combinations thereof. The solubility enhancing additive may also be selected from quaternary ammonium salts, ionic liquids, chlorinated and non-chlorinated organic solvents which solubilize iodine, polyols, and combinations of any of the above. The amount of this solubility enhancing additive is preferably within a range of from 0.1 percent by weight percent (wt %) to 50 wt %, more preferably from 1 wt % to 25 wt % and still more preferably from 2.6 wt % to 10 wt %, each wt % being based upon combined weight of additive(s) and water included in, or serving as, the reaction medium. An alternate means of expressing additive amount is a molar ratio of iodine to additive ($I_2$:additive) within a range of from 1:0.1 to 1:20, more preferably 1:0.5 to 1:10, and still more preferably from 1:1 to 1:4. It is noted that the same compound cannot serve as both the catalyst and the solubility enhancer, given the fact that the catalyst is an acid (i.e., it ionizes at least partially in an aqueous solution by losing one proton), whereas the possible additive selections are not, with the exception of lithium iodide. If lithium iodide is selected as both the solubility enhancing agent and the catalyst, it may be desirable to use an amount representing a combination of the amount for the catalyst and the amount for the solubility enhancing agent.

Temperature parameters employed in the invention may vary within a range of from 50° C. to 250° C., but are preferably from 100° C. to 210° C. Those skilled in the art will be aware that certain temperatures may be preferably combined with certain molar ratios of material and catalyst to obtain optimized olefin yield. For example, a temperature of at least 180° C. combined with a molar ratio of material to iodine atoms of 6:1 may yield, in some embodiments, especially good yields. Other combinations of temperature and ratio of moles of material to moles of iodine atoms may also yield desirable results in terms of conversion of material and selectivity to desired alkenes. For example, with an excess of HI, temperature may be varied especially within the preferred range of 100° C. to 210° C., to obtain a range of selectivity and conversion percentage. Processing at lower temperatures is another embodiment.

In certain particular embodiments the conditions may also include a varying amount of reaction time, typically within a range of from 1 hour (h) to 10 h. While a time longer than 10 h may be selected, such may tend to favor formation of byproducts such as those resulting from a reaction of the olefin with one or more of the reactants. Byproduct formation may be more prevalent in a batch reactor than in a continuous process. Conversely, a time shorter than 1 h may reduce olefin yield. Those skilled in the art will be aware that alteration of any parameter or combination of parameters may affect yields and selectivities achieved.

Gaseous hydrogen used in the invention may be in essentially pure form, but also may be in mixtures including, for example, carbon dioxide, carbon monoxide, nitrogen, methane, and any combination of hydrogen with one or more the above. The hydrogen itself may therefore be present in the stream in an amount ranging from 1 weight percent (wt %) to 100 wt %. The hydrogen or mixture including hydrogen is useful in the present invention at a pressure sufficient to promote conversion to the olefin. The pressure is desirably autogenous or may range from 1 psig (~6.89 KPa) to 2000 psig (~13.79 MPa), and preferably from 50 psig (~344.5 KPa) to 200 psig (~1.38 MPa). In many embodiments hydrogen pressures in excess of 2000 psig (~13.79 MPa) provide little or no discernible benefit and may simply increase cost of the process.

The inventive process may be accomplished using many of the equipment and overall processing parameter selections that should be generally and easily discernible by those skilled in the art. According to processing parameters selected, it may be desirable or necessary to include in the aqueous reaction medium a proportion of a liquid reaction medium in supplement to the water; however, water alone may be used in preferred embodiments. In general, the greater the proportion of water, the greater the advantage of using the solubility enhancement of the present invention. Any of the "materials," as defined hereinabove, may function as both the compound to be converted and as additional liquid reaction medium, but it is preferred that water represents at least 25 weight percent (wt %), more preferably at least 50 wt %, and most preferably at least 75 wt % of the combined total of reaction medium including any supplemental liquid reaction medium. In one embodiment, a carboxylic acid that contains from 4 carbon atoms to 20 carbon atoms, preferably from 8 carbon atoms to 16 carbon atoms, may be selected as a supplemental liquid reaction medium. Other organic solvents, such as polyols and dialkyl ethers, may also be supplementally selected. Where the material selected for conversion is a polyol, it may be desirable in some non-limiting embodiments for the polyol to be sufficiently miscible in the carboxylic acid that a reaction between the carboxylic acid and the polyol esterifies at least some of the polyol. This facilitates the conversion of the polyol to an olefin.

A particular advantage of the invention is that inclusion of the solubility enhancing agent increases the effect, i.e., the measured productivity, of the catalyst, which increases the conversion of the vicinal material(s). In particular and non-limiting embodiments of the invention, the solubility-enhanced catalysts of the invention exhibit a solubility that is increased by a factor of at least two-fold. In preferred embodiments the increase is by an even greater factor, of three-fold, four-fold, or even more. This means that the solubility of the iodine-based catalyst may be increased to at least 0.0022 moles of iodine atoms per liter of water at 20° C., and in some cases to at least 0.0033 or 0.0044 moles on the same basis. This leads to increased productivity of the catalyst and overall increased yields, as calculated using Equation 4 hereinbelow. Selectivities may also be altered thereby.

EXAMPLES

General Experimental Procedure

Use a 300 milliliter (mL), High Pressure HASTELLOY™ C-276 Parr reactor with a glass insert as a reaction vessel. Charge 90 mL of deionized (DI) water or acetic acid into the reactor. Add a known amount of ethylene glycol (EG) (S.D. Fine-Chem Ltd.), 1,2-propylene glycol (PG) (Merck) or glycerol (S.D. Fine-Chem Ltd.) to the water or acetic acid. Add 4 mL of a 55% (weight/weight) aqueous solution of hydroiodic acid (HI) (Merck) or 3.73 gram (g) $I_2$ (S.D. Fine-Chem Ltd.) to the reactor, then close the reactor and mount it on a reactor stand. Flush void space within the reactor two times with gaseous nitrogen (200 psig, ~1.38 MPa). Feed $H_2$ into the reactor up to a pressure of 500 psig (~3.45 MPa) and heat reactor contents, with stirring at a rate of 1000 revolutions per minute (rpm) up to a temperature of 210° C. Add sufficient additional $H_2$ to the reactor to increase pressure within the reactor up to 1000 psig (~6.89 MPa). After 45 minutes of reaction time, remove a sample of vapor phase within the reactor using a gas sampling vessel. Analyze the sample via gas chromatography (GC) (Agilent 7890 with two thermal conductivity detectors (TCDs) and one flame ionization detector (FID)). Use a PoraPlot™ Q (Varian™ CP7554) column to separate carbon dioxide ($CO_2$), olefins and alkanes. Use a CP Wax (Varian™ CP7558) column to separate oxygenates and a molecular sieve (Molsieve™) (Varian™ CP7539) column to separate hydrogen, nitrogen and lower hydrocarbons. Allow the reaction to continue for 6 hours, intermittently repressurizing the reactor with additional $H_2$ (1000 psig (~6.89 MPa)) to make up for consumption of $H_2$ during the reaction.

Calculate mole percent (mol %) conversion of material to olefin from vapor phase composition data according to the following equation:

$$\text{mole \%} = \left[\frac{\frac{\text{vol \%}}{100} \times \frac{\text{total pressure}}{14.7} \times \frac{\text{volume of gas}}{22400}}{\text{moles of material}}\right] \times 100 \qquad \text{[Equation 4]}$$

Comparative Example A

Using the above General Experimental Procedure with 0.20 moles of ethylene glycol (EG), 0.029 moles of HI, a temperature of 180° C. and a time of 5 h, effect a 5% conversion of EG with a product stream selectivity of 75 percent by weight (wt %) ethylene, 23 wt % ethane and 2 wt % $CO_2$, each wt % being based upon total product stream weight.

Comparative Example B

Replicate Comparative Example A, but decrease the amount of EG to 0.19 mole and increase the temperature to 210° C. This results in a 31% conversion of EG with a product stream selectivity of 86 wt % ethylene, 7 wt % ethane and 7 wt % $CO_2$, each wt % being based upon total product stream weight.

Example 1

Replicate Comparative Example B, but decrease the amount of EG to 0.18 mole, substitute 0.015 mole of $I_2$ in place of the HI, extend the time to 6 h, and add 0.015 moles of potassium iodide (KI) as the solubility enhancing agent to the deionized (DI) $H_2O$. In addition, allow intermittent release of gas phase. When the gas phase ethylene concentration reaches 33 volume % (vol %) of EG, cool reactor to 35° C. and release all gaseous components. Start the experiment as before and continue gas releases as and when required. This Example 1 effects a 36% conversion of EG with a product stream selectivity of 99 wt % ethylene and 1 wt % ethane, each wt % being based upon total product stream weight.

Example 2

Replicate Example 1, but increase the amount of EG to 0.20 mole and the amount of KI to 0.06 mole. This Ex 2 effects a 57% conversion of EG with a product stream selectivity of 86 wt % ethylene, 2 wt % ethane and 12 wt % $CO_2$, each wt % being based upon total product stream weight.

Example 3

Replicate Example 2, but reduce the amount of EG to 0.18 mole and add 0.06 mole of potassium iodide to the water in the absence of hydrogen. This Example 4 effects 99% conversion of the EG with a product stream selectivity of 84 wt % ethylene and 16 wt % $CO_2$, each wt % being based upon total product stream weight.

The invention claimed is:

1. A process for preparing an olefin comprising:

subjecting a material to a reductive dehydroxylation in presence of an iodine-based catalyst comprising at least one iodine atom per molecule thereof, gaseous hydrogen, and an aqueous reaction medium to form an olefin;

performing the reductive dihydroxylation under conditions including a hydrogen pressure ranging from 1 psig to 2000 psig, a temperature ranging from 50° C. to 250° C., and a ratio of moles of the material to moles of iodine atoms in the iodine-based catalyst ranging from 4:1 to 27:1;

wherein the material is selected from the group consisting of a vicinal polyol, an ester of a vicinal polyol, and combinations thereof; and wherein the iodine-based catalyst has a partial solubility in the aqueous reaction medium and the partial solubility is enhanced by adding to the aqueous reaction medium a solubility enhancing agent.

2. The process of claim 1 wherein the iodine-based catalyst has a solubility in the aqueous reaction medium, in the presence of the solubility enhancing agent, that is greater than 0.0011 mole of iodine atoms per liter of water at 20° C.

3. The process of claim 1 wherein the iodine-based catalyst has a solubility in the aqueous reaction medium, in the presence of the solubility enhancing agent, that is at least 0.0022 mole of iodine atoms per liter of water at 20° C.

4. The process of claim 1 wherein the solubility enhancing agent is selected from the group consisting of potassium iodide, sodium iodide, lithium iodide, quaternary ammonium salts, ionic liquids, chlorinated and non-chlorinated organic solvents, polyols, and combinations thereof.

5. The process of claim 1 wherein the solubility enhancing agent is potassium iodide.

6. The process of claim 1 wherein an amount of the solubility enhancing agent ranges from 0.1 weight percent to 50 weight percent, based upon the combined weight of the solubility enhancing agent and the aqueous reaction medium.

7. The process of claim 1 wherein an amount of the solubility enhancing agent ranges from 1 weight percent to 25 weight percent, based upon the combined weight of the solubility enhancing agent and the aqueous reaction medium.

8. The process of claim 1 wherein a percent conversion of the material is increased when the solubility enhancing agent is present in comparison with when the solubility enhancing agent is absent.

9. The process of claim 1 wherein the aqueous reaction medium is at least 75 weight percent water.

* * * * *